United States Patent
Kantrowitz et al.

(10) Patent No.: US 9,700,659 B2
(45) Date of Patent: Jul. 11, 2017

(54) CARDIAC ASSIST DEVICE, INSTRUMENTS, AND METHODS

(75) Inventors: Allen B. Kantrowitz, Miami, FL (US); Chris Mortis, Beverly Hills, MI (US)

(73) Assignee: VIADERM LLC, Ann Arbor, MI (US)

( * ) Notice: Subject to any disclaimer, the term of this patent is extended or adjusted under 35 U.S.C. 154(b) by 857 days.

(21) Appl. No.: 13/508,923

(22) PCT Filed: Nov. 9, 2010

(86) PCT No.: PCT/US2010/056027
§ 371 (c)(1),
(2), (4) Date: Oct. 1, 2012

(87) PCT Pub. No.: WO2011/057264
PCT Pub. Date: May 12, 2011

(65) Prior Publication Data
US 2013/0131436 A1 May 23, 2013

Related U.S. Application Data

(60) Provisional application No. 61/259,473, filed on Nov. 9, 2009, provisional application No. 61/265,150, filed on Nov. 30, 2009.

(51) Int. Cl.
*A61M 1/10* (2006.01)
*A61M 1/12* (2006.01)
*A61B 17/072* (2006.01)
*A61B 17/115* (2006.01)
*A61B 17/00* (2006.01)
*A61B 17/32* (2006.01)

(52) U.S. Cl.
CPC ......... *A61M 1/1072* (2013.01); *A61B 17/072* (2013.01); *A61B 17/1155* (2013.01); *A61M 1/1037* (2013.01); *A61M 1/122* (2014.02); *A61B 17/07292* (2013.01); *A61B 2017/00778* (2013.01); *A61B 2017/07221* (2013.01); *A61B 2017/07278* (2013.01); *A61B 2017/07285* (2013.01); *A61B 2017/320052* (2013.01); *A61M 1/106* (2013.01)

(58) Field of Classification Search
CPC .... A61M 1/1072; A61M 1/122; A61M 1/106; A61M 1/1037; A61M 1/1043
USPC .................... 606/153, 143; 600/18
See application file for complete search history.

(56) References Cited

U.S. PATENT DOCUMENTS

| | | |
|---|---|---|
| 6,471,633 B1 | 10/2002 | Freed |
| 2004/0152945 A1 | 8/2004 | Kantrowitz et al. |
| 2007/0119902 A1* | 5/2007 | Vargas et al. ............... 227/180.1 |
| 2007/0265490 A1* | 11/2007 | Smith et al. .................... 600/18 |

* cited by examiner

*Primary Examiner* — Christopher D Koharski
*Assistant Examiner* — Jeremiah Kimball
(74) *Attorney, Agent, or Firm* — Avery N. Goldstein; Blue Filament Law PLLC

(57) ABSTRACT

A cardiac assist device is provided that can be deployed in any region of the aorta by minimally invasive techniques by the way of an inventive fastener that affixes the device to the aorta wall at the site of an aortonomy. The devices and methods described herein allow for improved patient outcome.

13 Claims, 12 Drawing Sheets

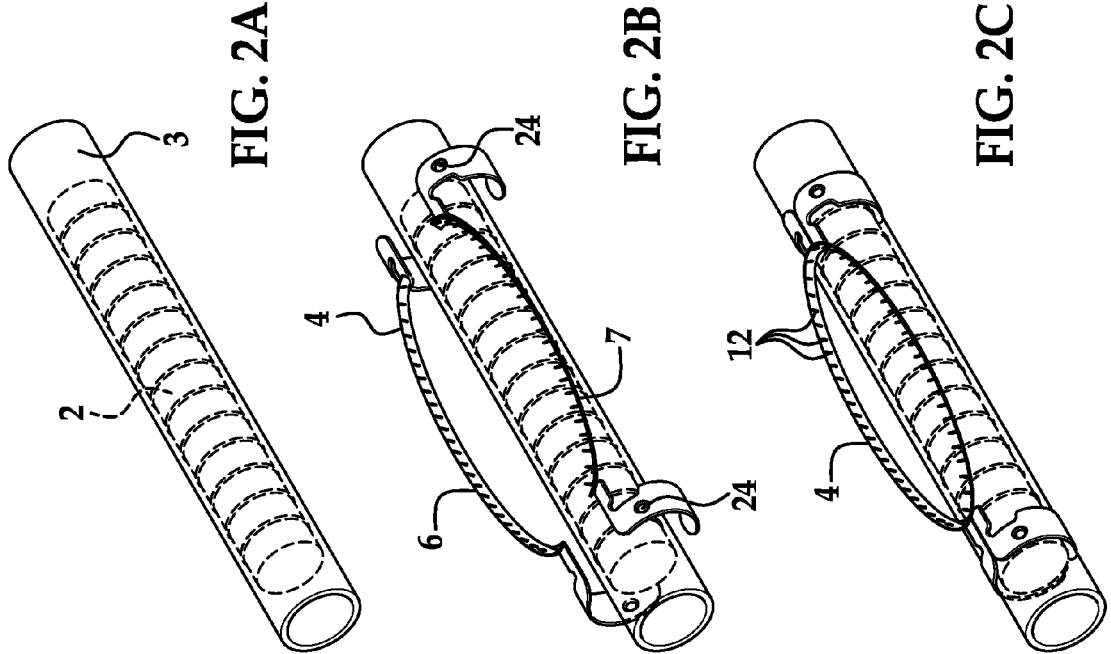
FIG. 2A
FIG. 2B
FIG. 2C
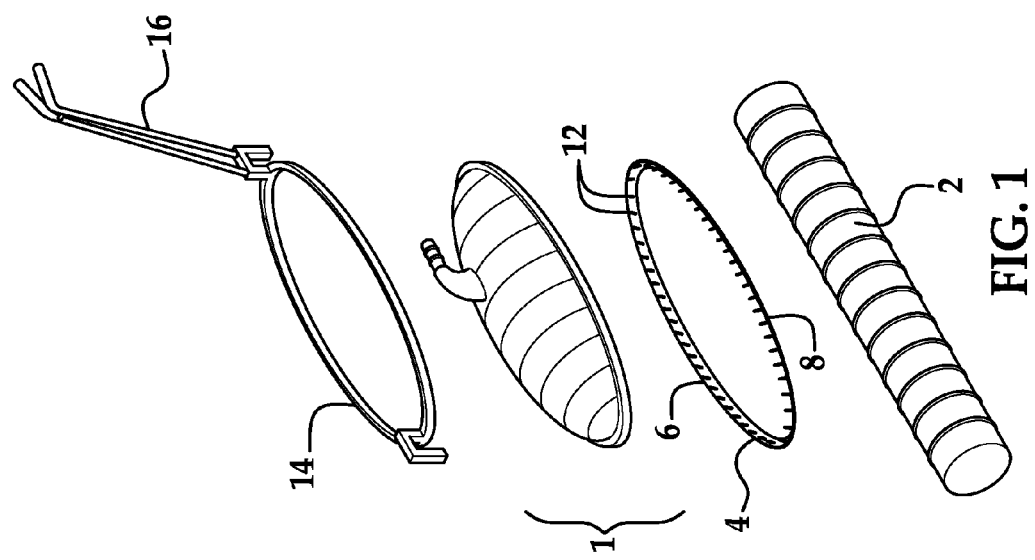
FIG. 1

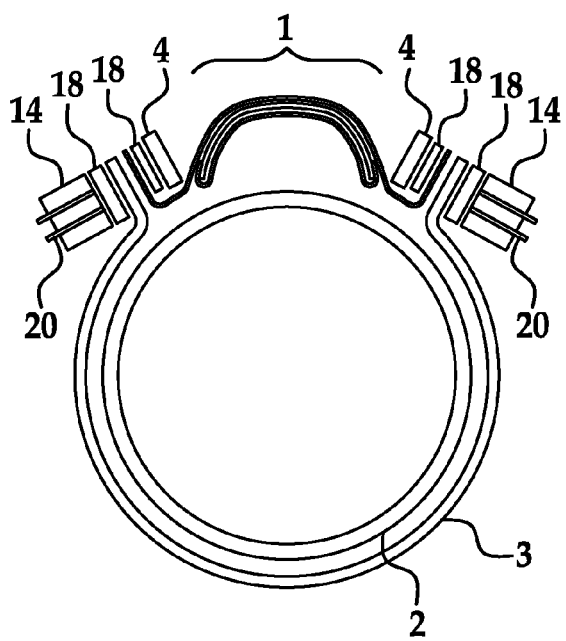
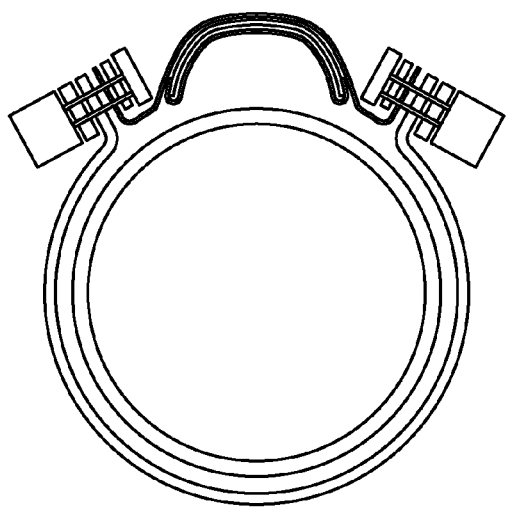
FIG. 3A  FIG. 3B
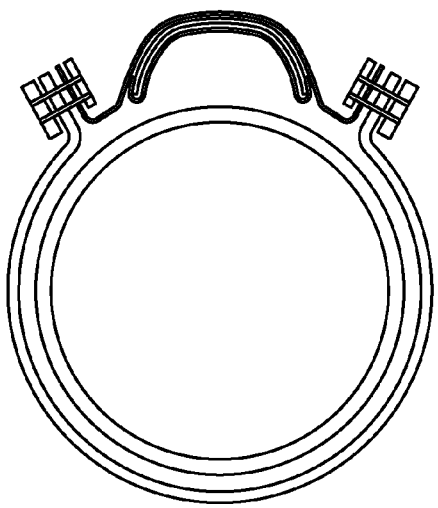
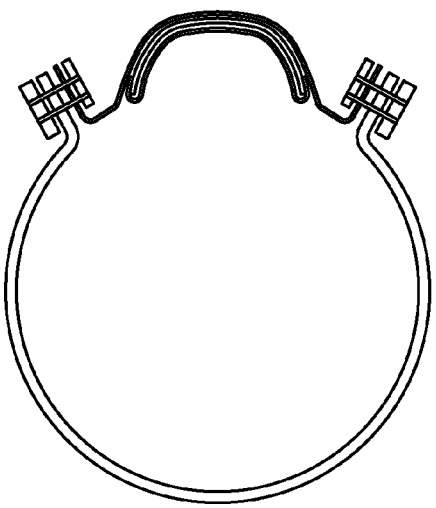
FIG. 3C  FIG. 3D

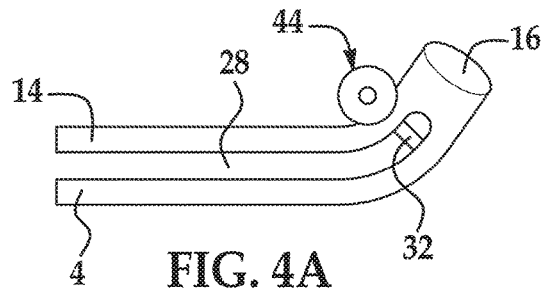
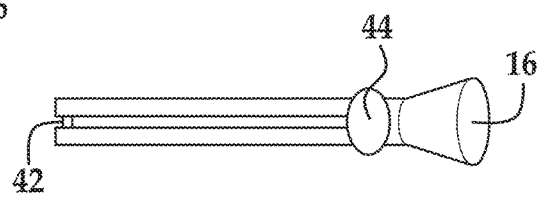
FIG. 4A   FIG. 4B
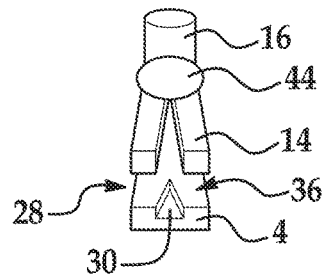
FIG. 4C
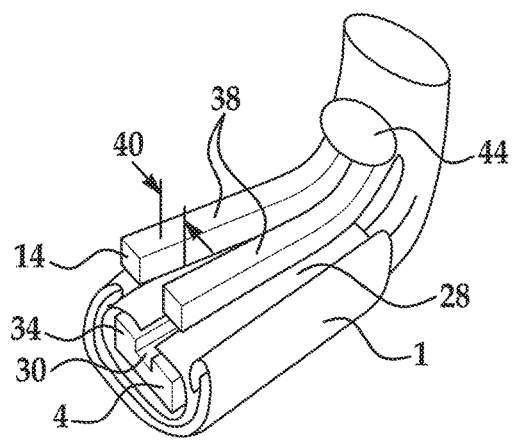
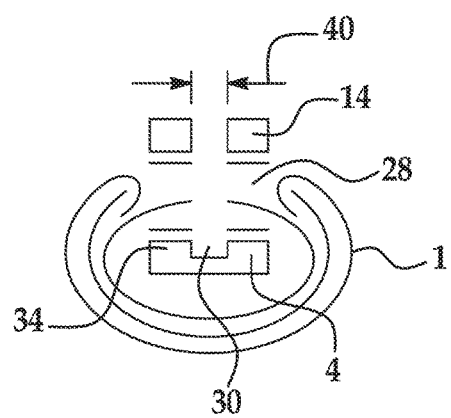
FIG. 4D   FIG. 4E

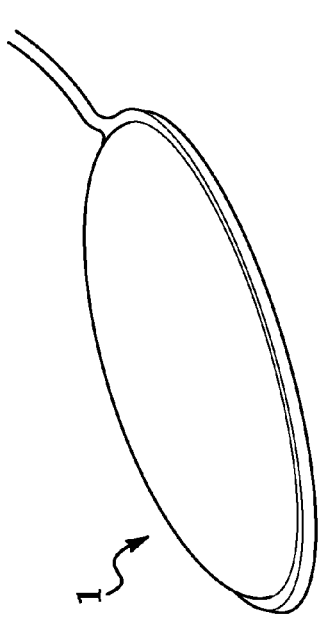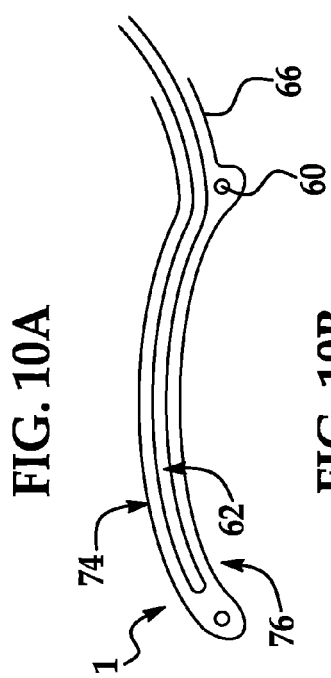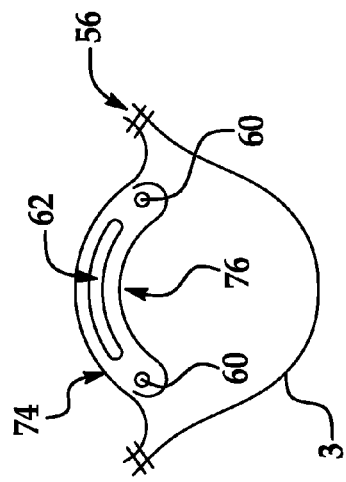
FIG. 10A  FIG. 10B  FIG. 10C
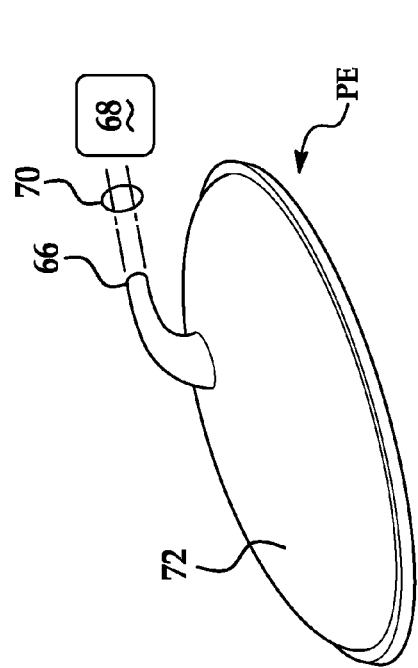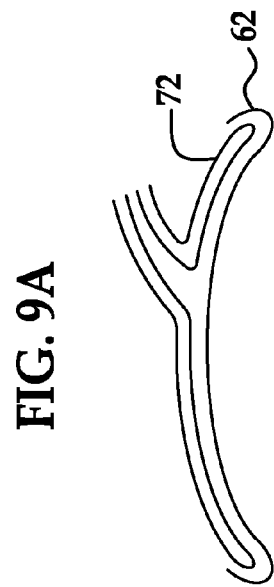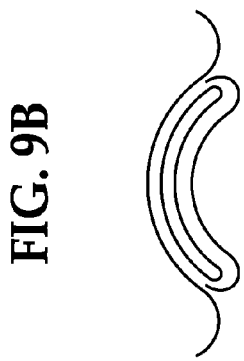
FIG. 9A  FIG. 9B  FIG. 9C

CARDIAC ASSIST DEVICE, INSTRUMENTS, AND METHODS

CROSS REFERENCE TO RELATED APPLICATIONS

This application depends from and claims priority to U.S. Provisional Application Nos. 61/259,473 filed Nov. 9, 2009 and 61/265,150 filed Nov. 30, 2009, the contents of each of which are incorporated herein by reference.

FIELD OF THE INVENTION

The present invention relates generally to cardiac assist devices. Inventive instrumentation and methods of delivery of cardiac assist devices are provided.

BACKGROUND OF THE INVENTION

The scarcity of human hearts available for transplant, as well as the logistics necessary to undertake heart transplant surgery, make an implantable cardiac assist device the only viable option for many heart patients. An aortic blood pump, for example, can be permanently surgically implanted in the wall of the aorta to augment the pumping action of the heart.

A known aortic blood pump includes a flexible bladder to be inflated and deflated in a predetermined synchronous pattern with respect to the diastole and systole of the patient to elevate aortic blood pressure immediately after aortic valve closure and decrease aortic blood pressure immediately before left ventricular ejection. Inflation and deflation of the bladder is accomplished by means of a supply tube connected to the bladder and to a percutaneous access device ("PAD"). The PAD is permanently surgically implanted in a patient's body to provide a through-the-skin coupling for connecting the supply tube to an extra-corporeal fluid pressure source. Electrical leads from electrodes implanted in the heart are likewise brought out through the skin by means of the PAD. The "R" wave of the electrocardiograph and the dicrotic notch are used to control the fluid pressure source to inflate and deflate the inflatable chamber in a predetermined synchronous relationship with the heart action.

The aortic blood pump acts to assist or augment the function of the left ventricle and is typically restricted to use in patients who have some functioning myocardium. The aortic blood pump does not need to be operated all the time, and in fact, can be operated periodically on a scheduled on-time, off-time regimen, or on an as-needed basis. Typically, the patient can be at least temporarily independent of the device for periods of one to four hours or more, depending on their heart function and level of activity. The general structure of known aortic blood pumps is a semi-rigid concave shell, and a flexible membrane that is integrally bonded to the outer surface of the shell, forming an inflatable and deflatable chamber. A fabric layer is then bonded over the exterior surface of the shell that projects clear of the shell forming a suture flange. These blood pumps have been tested and demonstrated to last a few million cycles.

A traditional cardiac assist device has an elongate bladder having a semi-rigid shell with walls of uniform thickness and a relatively thicker peripheral edge and a flexible, relatively thin membrane defining an inflatable chamber. At least one passage extends through the shell defining an opening in the inner surface of the shell. The flexible membrane is continuously bonded to the shell adjacent the peripheral side edge to define the enclosed inflatable chamber in communication with the passage.

Improvements on prior art blood pumps are disclosed in U.S. Publication No. 2007-0265490 A1, the entire contents of which are incorporated herein by reference. While these devices are improving both surgical success and clinical outcome, surgical implantation generally requires invasive techniques such as implantation via open thoracotomy. Thus, new instruments and methods are needed to improve surgical implantation that minimize the incision size and are amenable to rapid endovascular/thoracoscopic surgical techniques

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A fastener is provided for attaching a cardiac assist device to the aorta of a subject that that includes an anvil fixedly or removably attached to a staple magazine and a handle fixedly or removably attached to the anvil or the staple magazine, where the anvil, staple magazine or both are associated with a cardiac assist device prior to deploying the cardiac assist device. Any shape for an anvil or a staple magazine is operable herein illustratively including an elongate elliptical shape. The anvil, staple magazine, or both optionally include one or more embracers connected thereto wherein the embracers optionally include one or more securement points operable for associating said embracer with a shunt. The embracers may extend or are positioned beyond an aortotomy.

An anvil optionally includes two plateaus separated by a channel, each of the plateaus having a face oriented toward said staple magazine. Optionally, multiple staple shuttles are associated with a staple magazine such as two staple shuttles. A staple shuttle is optionally movably connected to the staple magazine, and optionally includes one or more knifes or other cutting instruments for creating an aortotomy. The cutting instrument optionally passes within the staple magazine, anvil, or portions thereof.

An anvil optionally includes two rectilinear extensions that are optionally associated at at least one end by a brace.

One or more alignment devices are optionally present that optionally removably connect the anvil to the staple magazine.

Also provided is a cardiac assist device for placement in an incision in an aorta such that part of the assist device after placement is in contact with blood passing through the aorta and by inflation and deflation provides left ventricular assistance. The assist device includes a foldable elongate housing including a flexible extra-aortic wall associated with a flexible endo-aortic membrane, a stiffener present within the housing and defining the outer dimensions thereof, and an airtight pumping chamber located within the housing and in fluid communication with a region external to the device. A percutaneous access device is optionally disposed external to the pumping chamber along an access channel that at least partially connects the pumping chamber to a fluid pump in fluid communication with the pumping chamber. A skirt is optionally provided having a first portion attached to the outer surface of the housing, and a second portion that is unattached to the outer surface of the housing, the unattached area forming a suture ring for attaching the assist device to the aorta of a patient. An overlayer nonadherent to scar tissue is optionally on an exposed surface of the skirt. A membrane edge is optionally preformed and looped with a maximal linear span of curvature that is greater than the maximal transverse linear extent of a support, wherein the housing includes a sufficient amount of air therein to form an air pocket intermediate between the support and said membrane during deflation of the assist device.

The assist device optionally has outer dimensions that are in an elongate form, optionally an elliptical form. In some embodiments, the assist device is associated with a fastener prior to deploying the assist device. Several orientations between a cardiac assist device and a fastener are operable including associations that will produce an everted anastomotic line or an overlap that does not produce an everted anastomotic line.

Also provided is a process of deploying a cardiac assist device wherein a cardiac assist device is stapled to an aorta using an inventive fastener. The assist device is optionally located at an ascending aorta, descending aorta, aortic arch, or a combination thereof. In some embodiments, an assist device is folded about the anvil prior to deployment. In some embodiments a shunt is used within the lumen of the aorta where the shunt is associated with an anvil via a cradle.

BRIEF DESCRIPTION OF THE DRAWINGS

FIG. 1 is a schematic of a fastener operable for use with a cardiac assist device and a shunt;

FIG. 2 is a representative example of an embodiment of an anvil with embracers that associate external to an aorta wall and optionally associate with a shunt positioned within the aorta;

FIG. 3 is a schematic of a fastener associated with a cardiac assist device as used to affix the cardiac assist device to the aorta;

FIG. 4. is a schematic of one embodiment of a fastener from a side view (A), top view (B), and end view (C), and as associated with one embodiment of a cardiac assist device illustrated from an angled perspective (D) and an end perspective (E);

FIG. 9 is a schematic of a cardiac assist device of the prior art;

FIG. 10 is a schematic of a supported inventive cardiac assist device operable to be deployed by an inventive fastener;

DETAILED DESCRIPTION OF EMBODIMENTS OF THE INVENTION

Figure 5A:
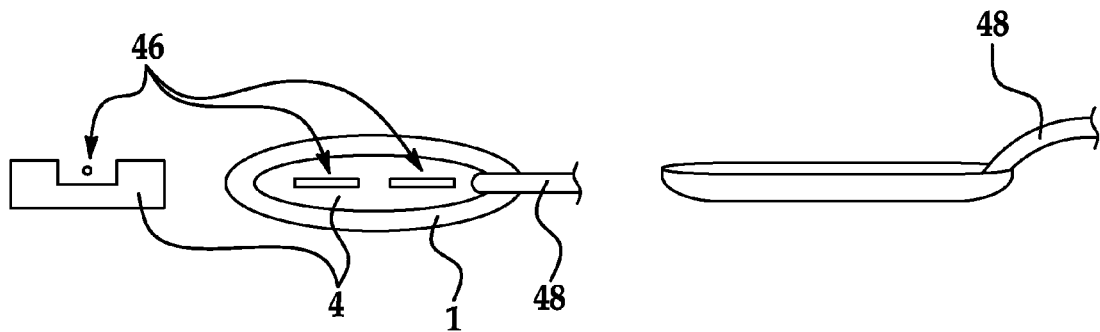
FIG. 5 is a schematic of one embodiment of a fastener illustrating (A) an endo-aortic component in the form of an anvil with included alignment devices, (B) an extra-aortic component in the form of a staple magazine, and (C) the associated endo- and extra-aortic components at the site of deployment of a cardiac assist device as positioned over a shunt.

The invention provides instruments for surgical implant of cardiac assist devices optionally by minimally invasive surgical (MIS) techniques. Thus, the invention has utility for surgical implant of cardiac assist devices. Also disclosed herein are improved cardiac assist devices that are amendable to insertion using the inventive fastener. As such, the invention has utility as a left ventricular assist device.

The description is directed to deployment of a cardiac assist device to the aorta of a patient. It is appreciated that the inventive fasteners are operable for the deployment of other devices such as a stent or catheter or for attaching an arterial or venus bypass to any artery or vein. It is to be understood that the present invention is not limited to particular embodiments described, as such may, of course, vary. It is also to be understood that the terminology used herein is for the purpose of describing particular embodiments only, and is not intended to be limiting. The numbering of the elements described herein and in the Figures are appreciated to be maintained therebetween.

It is appreciated that while a fastener is generally described with respect to staples, it is not limited as such. As opposed to staples, other means of attachment are operable herein illustratively including tacks, rivets, hooks, or any other mechanical fastener known in the art and operable with the invention. Types of staples or other attachment used are known by those of skill in the art. It is understood that the staples optionally exit the staple magazine perpendicularly toward the anvil so that they meet the anvil perpendicularly to its facing surface.

A basic cardiac assist device system includes a fluid pump; an inflatable bladder sutured into the wall of the aorta; an internal conduit connecting the bladder to a percutaneous access device ("PAD") where the PAD is a through-the-skin port that permits power, electrical signals and fluid (typically air) to pass between the fluid pump and the bladder; and an external drive unit powering and controlling the fluid pump. The PAD allows the implanted bladder to be operatively connected to or disconnected from the external drive unit. To inflate the bladder, pressurized air or other gas such as helium is supplied from the drive unit compressor (not shown). The air optionally flows from the compressor via an interconnect tube through a valve manifold in the drive unit to an external drive line running to the PAD and then through the implanted internal conduit to the bladder. Alternatively, an isolation chamber, separating the pressure (or vacuum) source from the air flowing to the pump, is used to isolate the subcutaneous portion of the pneumatic circuit from the supercutaneous portion.

A rigid cardiac assist device is implanted within the wall of the thoracic aorta. With the use of prior art instruments to implant the a cardiac assist device, a surgeon makes a longitudinal incision through the wall of the aorta, usually downward from a location just below the subclavian artery, and the device is placed within the incision and sewn firmly in position by sutures passing through a projecting suture ring flange. The inventive fastener optionally allows a surgeon to use MIS techniques to deploy a cardiac assist device while providing a secure joint between the device and the aortic wall. Alternatively, a fastener can be deployed to attach a rigid or semi-rigid backed cardiac assist device with improved speed due to rapid creation of an aortonomy, simultaneous or sequential stapling of the device to the aortonomy, and optionally simultaneous affixing nearly or all of the outer edge of the device to the aorta.

In several embodiments of an inventive fastener, surgical implant of a cardiac assist device includes an aortotomy and insertion of a temporary endovascular shunt within the lumen of the aorta 3 to allow blood flow during the procedure. As depicted in FIG. 1, the shunt 2 is optionally positioned via catheter-based endovascular techniques. An exemplary shunt operable herein is a thoracic aortic endograft designed to contain aortic blood flow in cases of thoracic aortic aneurysm. The endovascular shunt is intended only for temporary use during the cardiac assist device implantation procedure, but is not limited as such. Design features, such as expandable mesh stents and/or endovascular staples or tacks assure successful capture of the Aortic blood flow. Optional side arms or other modifications limit loss of blood flowing retrograde via the intercostal arteries. At the completion of the cardiac assist device implantation procedure, the endovascular shunt 2 is removed with special precautions designed to prevent damage to the flexible membrane of the cardiac assist device.

A shunt 2 optionally includes a graft material, such as polyethylene terephthalate or PTFE and a frame or support structure such as a balloon expandable or self-expanding stent structure. The shunt is optionally linear, but is optionally formed to define an angle, periscope or elbow shape. The shunt is optionally made from a soft and malleable material and is supported throughout its length with a self expanding structure that expands in a predictable and maintainable shape. As an alternative, the shunt is supported substantially only at its ends. This support is optionally in conjunction with one or more embracers 22 via transaortic securements 26 such as barbs, helix screws, sutures, or other securement known in the art.

A fastener is provided optionally in multiple parts that are optionally assembled at the site of assist device implantation prior to use, are preassembled, or are components of a unitary device. The inventive fastener optionally includes an anvil 4 that is optionally elliptically shaped. An anvil is optionally formed of a single piece or multiple pieces that are interconnected to form a stapling surface. FIG. 1 illustrates one embodiment of an anvil with a first side 6 and a second side 8 where the anvil 4 is depicted in a closed configuration. The first side 6 and second side 8 of an anvil 4 are optionally affixed at a first end by a solid joint, a rotatable or movable joint such as a hinge, clasps, other mechanical interlocks, or other configuration operable to associate the first side and second side of the anvil. FIG. 1 illustrates a configuration whereby the anvil 4 is affixed at a first end by a hinge joint 10. In some embodiments an anvil has a plurality of barbs 12 on one or multiple surfaces. The barbs 12 serve to stabilize or otherwise hold the aortic wall in an open configuration for attachment to a cardiac assist device by operation of a fastener.

A staple anvil 4 is provided removably or fixedly connected to a staple magazine 14. The staple anvil 4 receives one or more rows of aortic staples deployed from the staple magazine. The geometry of the anvil complements that of the staple magazine. The staple anvil is optionally manufactured as a single ring of an elliptical geometry accommodating the suture skirt of the cardiac assist device 1 (e.g. CardioVad®), or optionally it is subdivided into subsections that are assembled in situ by the operating surgeon. Optionally, the in situ assembly of the subsections is aided by hinges, clasps, or mechanical interlocks. The segmentation into subsections facilitates removal of the staple anvil at the completion of the implant procedure. Optionally, a length of pledget, to be included as a buttress within the cardiac assist device anastomotic line, is preloaded on to the face of the staple anvil.

The staple anvil includes a face oriented toward a staple magazine that has a plurality of staggered depressions shaped and dimensioned for forming the staples upon actuation of the fastener to affix a cardiac assist device to the aortic wall. The depressions optionally form a double row configuration. It is appreciated that a triple row, quadruple row, or single row of depressions are similarly operable. The orientation of the depressions is associated with the staple pattern used by the inventive fastener. The dimensions of the depressions are associated with the dimensions of the staples used.

An anvil 4 is connected, optionally removably, to a staple magazine 14 that is removably or fixedly attached to a handle 16 or other actuation device allowing a surgeon to trigger stapling of a cardiac assist device to the aorta. It is appreciated that a handle 16 is optionally removably or fixedly connected to an anvil or a combination of an anvil and staple magazine. Optionally, a fastener is a single piece that is delivered as a whole for use in attaching a cardiac assist device to the aortic wall. A fastener is optionally provided in three major components that are optionally assembled at the site of aortic incision: an anvil; a staple magazine; and a handle.

A staple magazine 14 carries one or more rows of aortic staples, optionally preloaded, that may be deployed in staggered rows. The staple magazine 14 is optionally manufactured as a single elongate shape optionally of elliptical geometry accommodating the skirt of a rigid or semi-rigid cardiac assist device, or it may be subdivided into subsections that are pre-assembled or assembled in situ by the operating surgeon. It is appreciated that the shape of the staple magazine and anvil are such that they may accommodate the outer geometry of a rigid or semi-rigid cardiac assist device or may be linear, elliptical, or other shape, for use with a foldable cardiac assist device. The in situ assembly of the subsections is optionally aided by hinges, clasps, or mechanical interlocks. The segmentation into subsections facilitates removal of the staple magazine at the completion of the implant procedure. In some embodiments, assembly of the fastener includes positioning of a pledget 18, illustratively made from polyethylene terephthalate (DACRON), surgical felt, or other acceptable material, between the fastener and the outer aortic wall and a second pledget 18 between the anvil and the cardiac assist device. It is appreciated that polyethylene terephthalate and surgical felt are but two of many materials operable for a pledget. Optionally, a pledget 18 to be included as a buttress within the cardiac assist device anastomotic line is preloaded on to the face of the staple magazine or anvil.

The position of the staple magazine 14 is optionally on the aortic aspect of the anastomotic line and the position of the staple anvil is optionally on the cardiac assist device aspect of the anastomotic line. Alternatively, the position of the staple magazine is on the cardiac assist device aspect of the anastomotic line and the position of the staple anvil is optionally on the aortic aspect of the anastomotic line. For simplicity, only the first of these configurations is depicted in FIG. 3.

Optionally, the component that is positioned on the aortic aspect of the anastomotic line is manufactured with small hooks, barbs 12 (shown as on the anvil in FIG. 1) or other devices or accommodations to help the surgeon maintain the everted position of the margin of the aortic wall aortotomy. In some embodiments the staple magazine includes the small hooks, barbs, or other accommodations.

A staple deployment mechanism, illustratively referred to herein as a handle and depicted at 16 in FIG. 1, is provided removably or fixedly attached to the staple anvil, the staple magazine, or both. As depicted in FIG. 3, after the surgeon has brought together the cardiac assist device aortotomy margins, staple magazine 14, and anvil 4, the handle, optionally in the form of a pistol grip, specialized handle or other device, is used by the surgeon to deploy the aortic staples 20 from the staple magazine 14 towards the staple anvil 4. (FIG. 3B) It is appreciated that all or a portion of the staples are deployed simultaneously or sequentially. The components of the fastener are optionally then dis-assembled and removed from the patient. (FIGS. 3C and D).

The staple magazine and staple anvil are optionally associated by a pivotable joint shown at 10 in FIG. 1 at the first end of the two components. The pivot joint 10 is optionally a hook and slot configuration to create a joint that will not expand beyond a certain threshold. The assembly of the inventive fastener optionally includes forming the pivot joint at the distal end and bringing the anvil and the staple magazine together at the proximal end. The joint at the proximal end is optionally forced closed by the staple deployment mechanism causing the staples to transfer from the staple magazine toward the anvil for closed staple formation along the entire length of the staple magazine. The cardiac assist device is optionally affixed to the aortic wall throughout its external circumference with a single effort of the surgeon.

As depicted in FIG. 2, an inventive fastener optionally includes one or more embracers or struts (collectively 22) that straddle those segments of aorta being engaged internally by the anchoring segments of the endo-aortic-shunt. The embracers 22 are optionally extensions of the staple magazine or the anvil 4. The embracers are optionally extensions of the portion of the inventive fastener that is present on the aortic aspect of the anastomotic line. This interaction provides numerous advantages over other prior art mechanisms including the improved security of aortic control necessary for a minimally invasive surgical (MIS) approach provided by the interaction between an extra-aortic component of the fastener and the endo-aortic shunt. The embracers 22 rest on the outer wall of the aorta 3 optionally external to the regions on the endo-aortic shunt 2 used to secure the shunt to the aorta providing a bracing effect and greatly improved security for both the shunt and fastener.

One or more embracers 22 optionally rest at regions extending beyond the aortotomy terminal ends optionally where the shunt 2 is anchored within the aorta lumen so as to prevent leakage during a surgical procedure. The one or more embracers 22 optionally include a plurality of pre-positioned securement points 24, illustratively holes, for attachment to a shunt 2 through the aortic wall preventing both slippage of the shunt during the insertion of a cardiac assist device and secure positioning of the fastener with respect to the aortotomy. A shunt 2 is optionally tacked to one or more embracers 22 by helical tacks, screws, sutures or other securing mechanism known in the art. It is appreciated that a GORE-TEX® mesh 18 is optionally tacked at the same location. This inventive configuration maintains positioning of the surgical complex irrespective of aortic movement from either surgical manipulation or changes in intra-aortic pressure during ventricular cycles.

The embracers 22 optionally include a plurality of grooved or recessed regions that serve to align the other components of the fastener. In some embodiments, the embracers 22 are present as a portion or removably attached to staple magazine. The grooves serve to orient the staple anvil 4 in position to ensure accurate and secure stapling of the assist device to the aorta. Optionally, the embracers 22 are a portion of or are removably attached to an anvil 4 whereby the grooves orient the positioning of the staple magazine 14 for subsequent accurate and secure stapling of the assist device to the aorta.

It is appreciated that the staple magazine, anvil, embracers, or staple deployment mechanism are fabricated from virtually any biocompatible material, including, but not limited to, stainless steel and its alloys, titanium alloys (i.e., nickel-titanium), polymers (i.e., polyethylene and copolymers thereof, and the like), other suitable material known in the art, or combinations thereof.

In some embodiments an inventive fastener system has a linear orientation illustratively as depicted in FIG. 4. A linear fastener system is optionally used to employ a foldable cardiac assist device optionally through a linear aortotomy. A linear fastener is optionally a plurality of components that are assembled at the site of aortotomy or at another remote location, or is a pre-assembled or single unit. In some embodiments, a fastener is a single unit including a staple anvil 4 that is associated at a proximal or second end with a staple magazine 14 whereby the length of the substantially linear staple anvil 4 and staple magazine 14 form a slot 28 that is optionally of uniform width. The slot 28 is of sufficient width such that at least an inventive cardiac assist device 1 and aorta wall 3 are accepted within the slot or portion thereof. (FIG. 4D) Alternatively, the staple magazine and the anvil are associated by a hinge or other device at the proximal end such that the slot is opened or closed similar to a jaw. The staple anvil is optionally in a position oriented at an endo-aortic aspect relative to the staple magazine with respect to the fastener orientation when employed at the site of aortotomy. As such, when the inventive fastener is used, the anvil extends along the inner surface of the aorta wall.

In some embodiments, a staple anvil has two plateaus 34, optionally substantially linear, that extend from at or near the proximal end to at or near the distal end of the anvil 4 whereby the separation forms a channel 30. The channel 30 is optionally less than 1 mm in width. The channel 30 is optionally of sufficient width to allow a cutter 32, such as a blade or knife, to pass through the channel. Each plateau 34 optionally includes a face oriented toward a staple magazine each of which have a plurality of staggered depressions 36 that are shaped and dimensioned for forming the staples upon actuation of the fastener to affix a cardiac assist device to the arotic wall. The depressions optionally form a double row configuration. It is appreciated that a triple row, quadruple row, or single row of depressions are similarly operable herein. The orientation of the depressions is associated with the staple pattern used by the inventive fastener. The dimensions of the depressions are associated with the dimensions of the staples used.

Alternatively, the staple anvil 4 forms two rectilinear extensions that are separated from one another by a space. The space is optionally uniform in width and is optionally less than 1 mm. The space is optionally of sufficient width to allow a surgical blade or other cutting apparatus or source to pass through the channel. A brace is optionally positioned at the distal end of the anvil to provide additional support for the extensions to minimize separation or closure of the space during the stapling process.

A staple magazine 14 is optionally two elongated staple extensions that form a magazine slot 40 therebetween. The dimensions of the staple magazine slot 40 are optionally coincident with the dimensions of the channel 30 in the anvil.

The length of the staple magazine 14 is optionally similar to the staple anvil length, but is optionally longer or shorter. The distal end of the staple magazine optionally includes a brace 42 to provide additional support for the extensions 38 to minimize separation or closure of the space during the stapling process. Each extension carries one or more rows of pre-loaded aortic staples deployed in staggered rows.

The proximal ends of the anvil 4 and the staple magazine 14 are optionally associated with a hinge or other movable connection so that the distal ends are separable for the pre-loading of a cardiac assist device to form an open jaws-like configuration. The anvil and the staple magazine are then optionally moved back into position to hold the cardiac assist device in position optionally by frictional fit.

An inventive fastener optionally includes one or more staple shuttles 44 that move along or through the slot between the staple magazine extensions 38 to deploy staples at the desired locations. A staple shuttle 44 optionally includes a cutter 32 such as a surgical blade, knife, laser, thermal cutter, or other instrument for creating or extending an aortotomy. The cutter 32 optionally extends between the staple magazine extensions into the channel 30 of the anvil. These embodiments allow support of the blade at both the exterior and interior sides of the aorta.

A fastener optionally includes an activation component 16, in the form of a pistol grip, specialized handle or other device used by the surgeon to deploy aortic staples from the staple magazine 14 towards the staple anvil 4. The three components of the fastener are then optionally dis-assembled and removed from the patient.

A linear fastener such as the embodiment depicted in FIG. 4 provides numerous advantages. The surgeon is able to create a small incision in the aorta that need only be of sufficient size to accept insertion of an endovascular shunt and allow positioning of the inventive fastener. The entire length of the final aortotomy need not be made until the shunt, fastener, and assist device are properly positioned. The full length aortotomy is then created by the blade associated with the staple shuttle so that a near simultaneous incision and stapling of the assist device to the site of cardiac assist device deployment is achieved minimizing the need for support or eversion of the aortic wall for delivery of the assist device. In some embodiments, the staples are deployed ahead of the blade so that when the aorta is cut, the edges of the incision are already associated with the assist device negating the need for additional support or guidance of the staples during deployment.

As used herein, the term "deploy," deployment," or "deploying" are defined as an action whereby a staple is moved from a loaded configuration to a final configuration whereby at least two elements, illustratively a cardiac assist device and an aortic wall, are associated, or in the case of a cardiac assist device the positioning of the device in a location and orientation so as to be operable as intended.

Figure 5B:
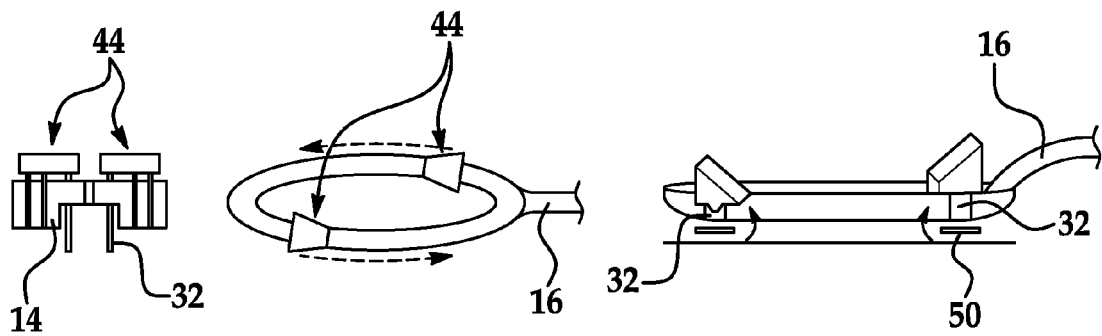
Figure 5C:
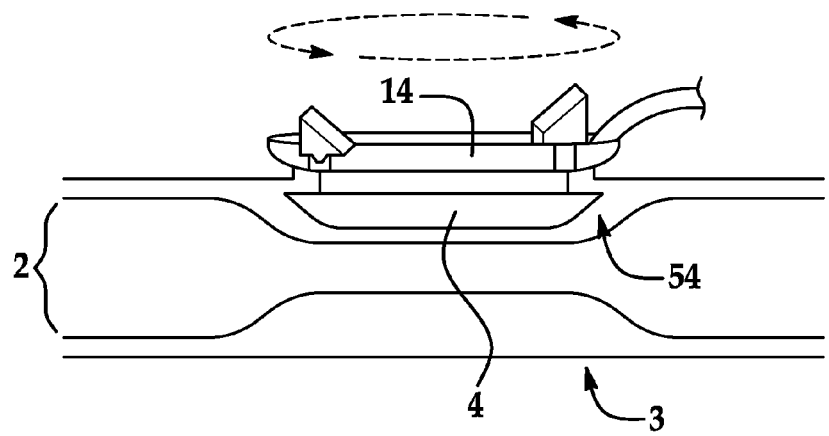
Figure 6A:
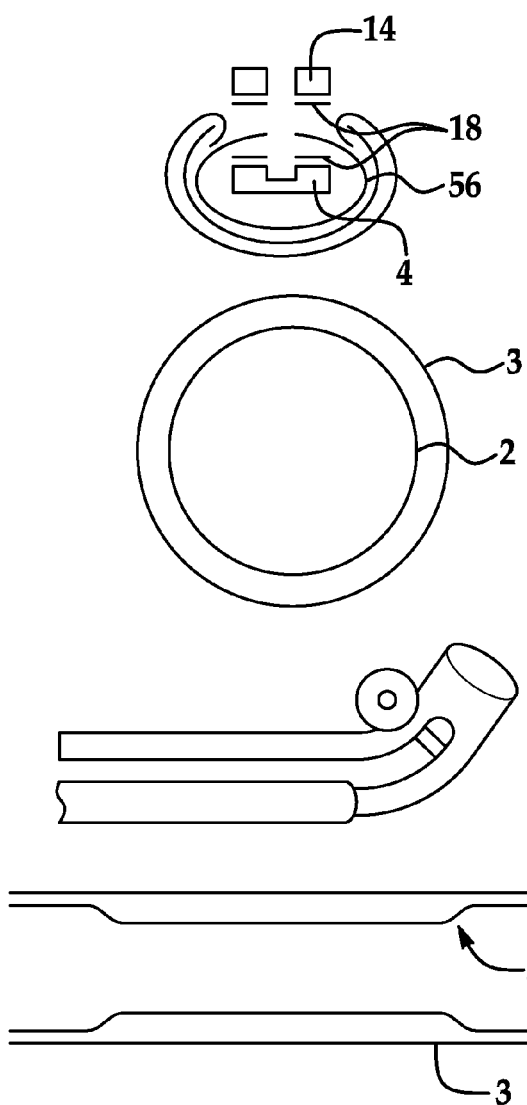
FIG. 6 illustrates one example of deploying a cardiac assist device with an inventive fastener where the cardiac assist device is pre-loaded onto an endo-aortic portion of a fastener and positioned in the region of a shunt (A), the fastener is then inserted through a small incision into the aorta at the region of the shunt (B) until the entire cardiac assist device is within the lumen of the aorta (C), the engagement of a staple shuttle to simultaneously create an aortonomy and affix the cardiac assist device to the wall of the aorta (D), subsequent removal of the fastener (E), and an end perspective view of the attached cardiac assist device (F)
Figure 6B:
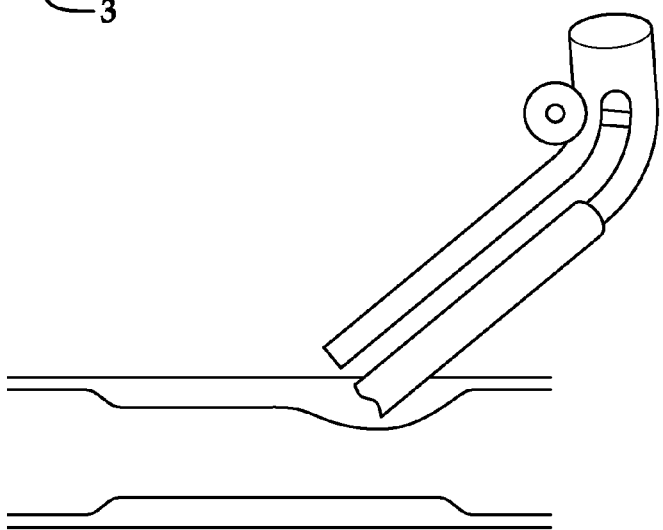
Figure 6C:
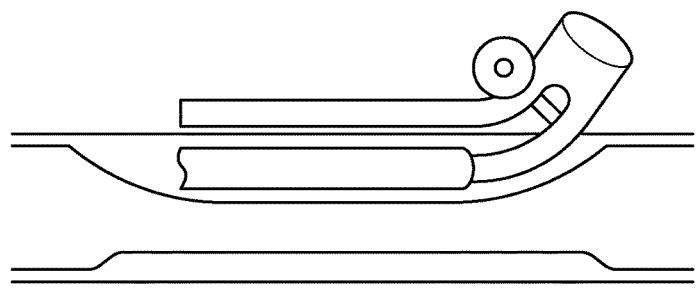
Figure 6D:
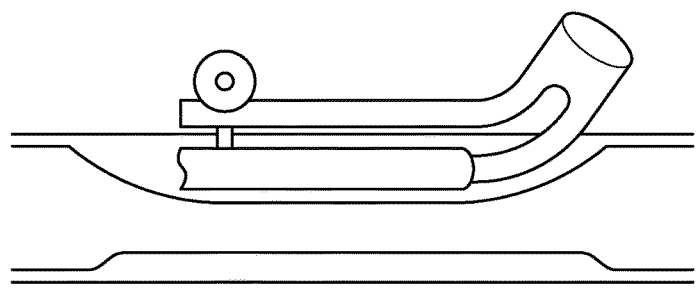
Figure 6E:
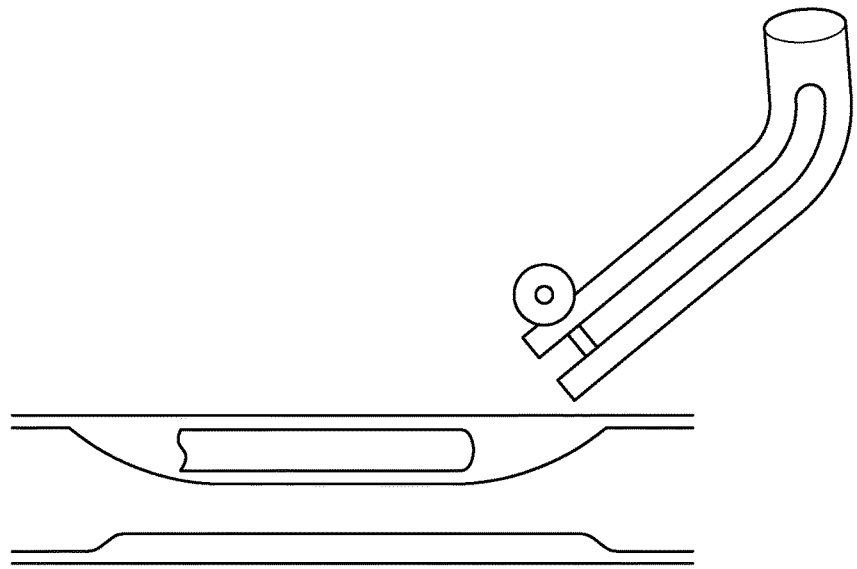
Figure 6F:
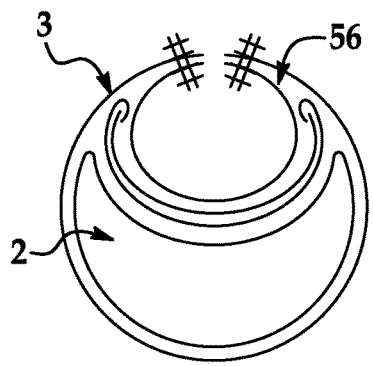

In some embodiments, a fastener is optionally introduced in two sections as depicted in FIG. 5. The endo-aortic component, optionally configured of an anvil 4 carrying the cardiac assist device 1, is delivered to the thoracic descending aorta via a catheter-based endovascular technique. The description herein refers to an endo-aortic component as an anvil and an extra-aortic component as a staple magazine for illustrative purposes only and are not meant as a limitation thereon. It is equally appreciated that an endo-aortic component or extra-aortic component may be an anvil, a staple magazine, combinations thereof, or fractions thereof.

The endo-aortic component optionally includes an elliptical plateau encircling the outer edge of the endo-aortic component. The elliptical plateau surrounds an optional channel or depression within the endo-aortic component. An endo-aortic component is optionally a substantially flat surface or other shape operable for acting as an anvil.

As depicted in FIG. 5, an endo-aortic component channel 30 optionally includes one or more stowed alignment devices 46. It is appreciated that the stowed alignment devices need not be positioned within a channel. One or more alignment devices 46, illustratively pins, helical tacks, or other extensions, are optionally positioned at or near the terminal ends of the endo-aortic component, optionally positioned at or near the ends of the long axis of the endo-aortic component, and are used to pierce or otherwise traverse the aortic wall. The alignment devices are optionally positioned longitudinally along the central axis of the shape of an endo-aortic component. Optionally, an endo-aortic component has two, three, four, five, six or more alignment devices. In some embodiments, two stowed alignment devices are present on an endo-aortic component. It is appreciated that the alignment devices are stowed prior to deployment in any configuration that allows for compact packaging within the endo-aortic component and subsequent deployment. These alignment devices 46 are optionally in a stowed configuration when the endo-aortic component is introduced to the site of deploying a cardiac assist device.

An actuator 48 is optionally removably attached to an endo-aortic component. The actuator deploys the alignment devices 46 into an orientation such that each alignment device is able to pierce the aortic wall upon deployment. In some embodiments, the devices are deployed into a position that is substantially perpendicular to the longitudinal axis of the endo-aortic component. A locking mechanism 50 is optionally provided that locks the alignment devices 46 in a deployed position to prevent subsequent movement or other collapse of one or more of the alignment devices upon deployment. The locking mechanism 50 optionally engages one or more alignment devices 46 via a slot, hole, or other engagement mechanism 52. Following deployment of the alignment devices, the actuator 48 is optionally detached from the endo-aortic component.

The use of an endo-aortic component that can be delivered prior to, along with, or subsequent to delivery of the shunt removes the need for an "initial access" aortotomy needing incidental repair at the completion of the procedure. This is because the endo-aortic component is delivered to the implant site via an endo-vascular route rather than the extra-aortic route. In some embodiments, an endo-aortic component is associated with a shunt or positioned on a shunt by one or more cradles 54. A cradle 54 is optionally a ridge, depression, flange, or other structure associated with a shunt 2. In some embodiments, a shunt 2 is coupled to an endo-aortic component by a cradle prior to insertion into the site of cardiac assist device deployment.

An extra-aortic component, optionally a staple magazine 14 with a staple shuttle 44, is introduced via thoracoscopic MIS technique. The extra-aortic component has a position that is operable to align with the endo-aortic component, optionally via one or more alignment devices 46. The fastener then is assembled and activated attaching the cardiac assist device to the aortic wall. The extra-aortic component is optionally similarly dimensioned to the endo-aortic component such that the path used by one or more staple shuttles will travel along the shape of the endo-aortic component for proper stapling or attachment of the cardiac assist device. Optionally, an extra-aortic component is elliptically shaped and includes an open centered slot.

The extra-aortic component optionally includes a locking mechanism 50 for rigidly associating the extra-aortic component to the endo-aortic component via the alignment devices 46. A lock 50 is optionally a pin that slides into a slot 52 in an alignment mechanism. Alternatively, the lock 50 creates a less than rigid, optionally flexible, association between the extra-aortic component and the endo-aortic component optionally to allow flex or other movement of the aorta or devices during deployment of the cardiac assist device.

Dual staple shuttles are optionally employed on an extra-aortic component. Dual staple shuttles activate the extra-aortic staple magazine and create an aortotomy, optionally an elliptical aortotomy. This allows the endo-aortic component of the fastener to be retrieved via the aortotomy and removed via the thoracoscopic MIS approach. It is appreciated that a single staple shuttle is optionally used and similarly allows recovery of the endo-aortic component via the aortotomy. Each staple shuttle optionally includes a knife or other cutting device such that travel of the staple shuttle along the outer circumference of the extra-aortic component simultaneously creates an aortotomy in the aortic wall and staples the cardiac assist device as each staple shuttle moves.

An extra-aortic component optionally includes one or more embracers substantially similar to embracers optionally associated with an anvil as described herein. The embracers optionally have one or more optional helical tack positions such that the embracers associate with the shunt providing additional rigidity between the shunt, the cardiac assist device, the endo-aortic component, and the extra-aortic component.

An illustrative process for deploying a foldable cardiac assist device to the aorta of a subject is depicted in FIG. 6. As used herein the term "subject" is meant to be an animal, illustratively a mammal. A subject is optionally a human, or non-human primate, equine, bovine, murine, pig, or any other animal with an aorta. A cardiac assist device with sufficient flexibility to be rolled or folded, optionally without a crease, is associated with an inventive fastener by preloading. (FIG. 6A) As defined herein, the term "associated with" with respect to a cardiac assist device and a fastener is meant to be an arrangement such that the fastener is capable of attaching the device to a target organ without substantial further adjustment of the relative positions of the device and the fastener. In some embodiments, the device is folded longitudinally while preserving the topologic relationships between the components of the device. The second portions (i.e. edges) of the anastomotic skirt of the assist device are positioned between the staple magazine extensions and the plateaus of the anvil. A first pledget is optionally positioned between each staple magazine and the assist device and a second pledget optionally between the anvil and the assist device. A small incision is made in the aorta to allow insertion of the endovascular shunt. After the shunt is in place, the fastener, with the preloaded assist device, is passed through the small incision and moved along the length of the shunt such that the anvil and cardiac assist device are on the inner aortic wall. (FIG. 6B) The staple magazine is positioned along the outer aortic wall. (FIG. 6C) The staple shuttle is then extended along the length of the staple magazine and anvil stapling the anastomotic skirt (or other attachment component) 56 of the assist device to the aortic wall as it moves. (FIG. 6D) As the staple shuttle moves from the proximal end to the distal end of the staple magazine, or visa versa, the associated knife creates a length of incision that defines the outer edges of the assist device when fully deployed. It is appreciated that the staple shuttle is optionally moved from the proximal end to the distal end creating an aortotomy and then retracted back toward the proximal end of staple magazine during stapling, or visa versa. Alternatively, a second row, or plurality of rows, of staples are optionally deployed while the staple shuttle is retracted back toward the proximal end of the fastener. In some embodiments, multiple staple shuttles are deployed to create two edges of a resulting aortotomy and engage staples to attach an assist device to the aortic wall. The fastener is then removed. (FIG. 6E)

Figure 7:
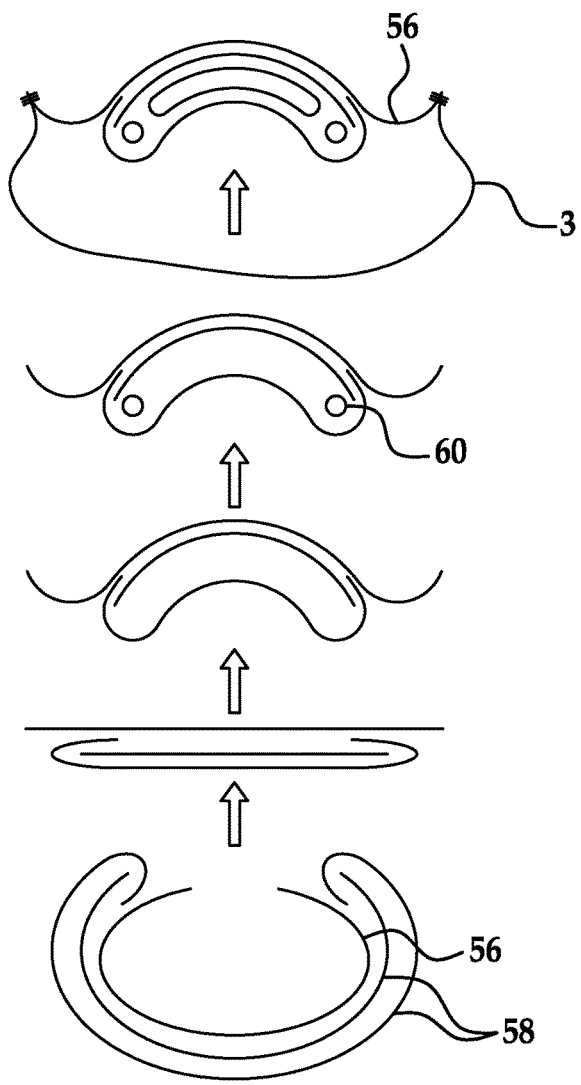
FIG. 7 illustrates an eversion sequence of a foldable cardiac assist device, insertion of a support and a pumping chamber.
Figure 8A:
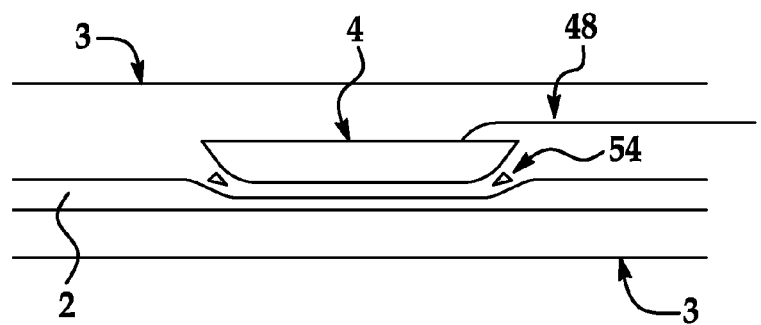
FIG. 8 illustrates the deployment of a cardiac assist device with one embodiment of a fastener whereby the endo-aortic component is in the form of an anvil with two alignment devices is positioned onto a shunt at the site of deploying a cardiac assist device (A), the actuator deploys the alignment devices (B) followed by expansion of the shunt such that the alignment devices puncture the wall of the aorta and extend beyond the outer surface of the aorta wall (C), an extra-aortic component in the form of a staple magazine with associated staple shuttles is inserted by minimally invasive techniques to the location of the shunt (D) and associated with the endo-aortic component by proper positioning of the alignment devices in the extra-aortic component (E), the staple shuttles simultaneously create an aortonomy and affix the cardiac assist device to the aorta (F) and the fastener is then removed in singular form through the resulting aortonomy (G), an access channel is then associated with the cardiac assist device (H, I) through which a support and pumping chamber are inserted into the housing of the cardiac assist device (J)
Figure 8B:
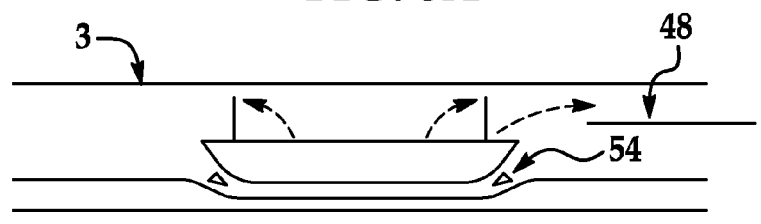
Figure 8C:
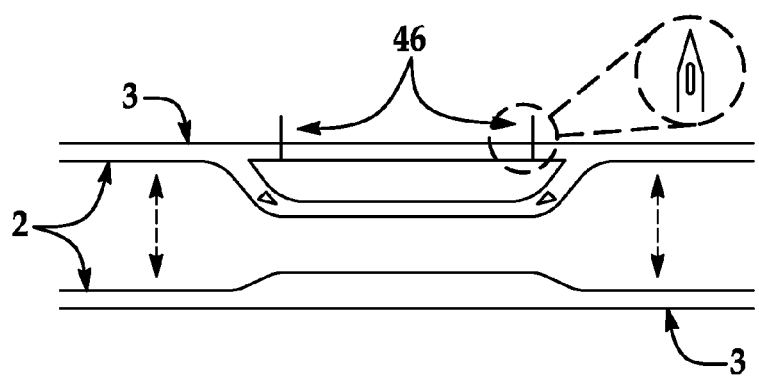
Figure 8D:
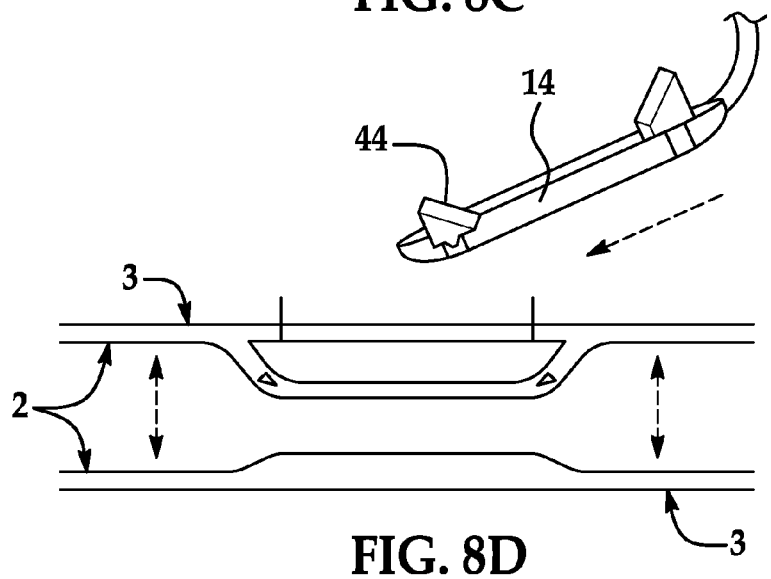
Figure 8E:
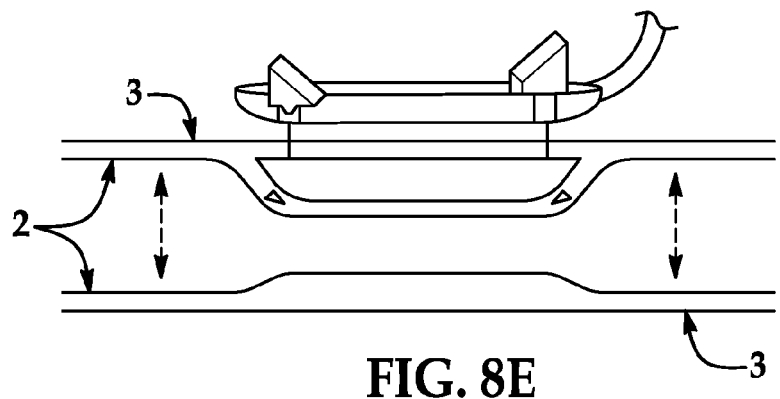
Figure 8F:
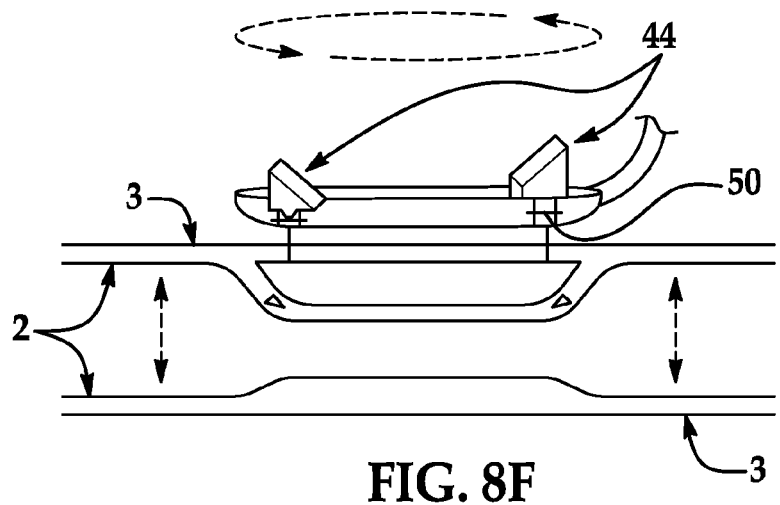
Figure 8G:
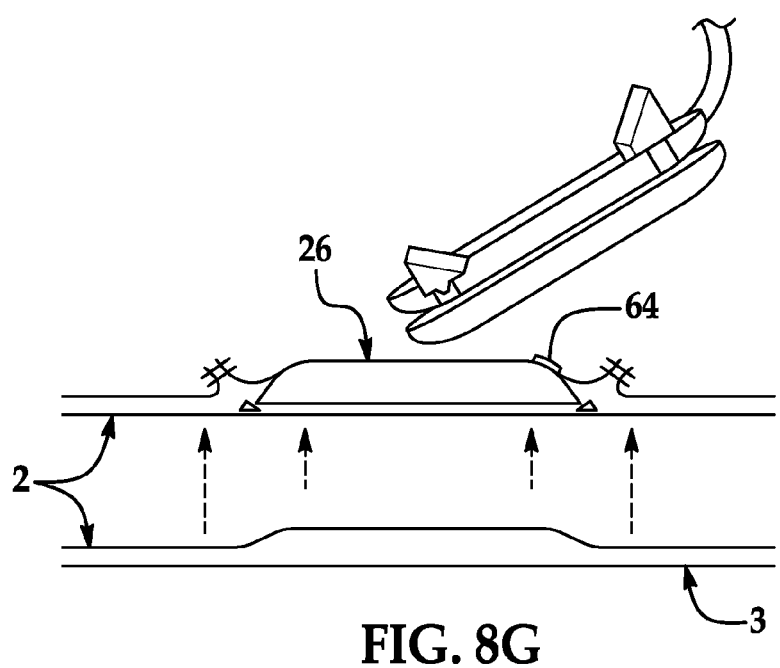
Figure 8H:
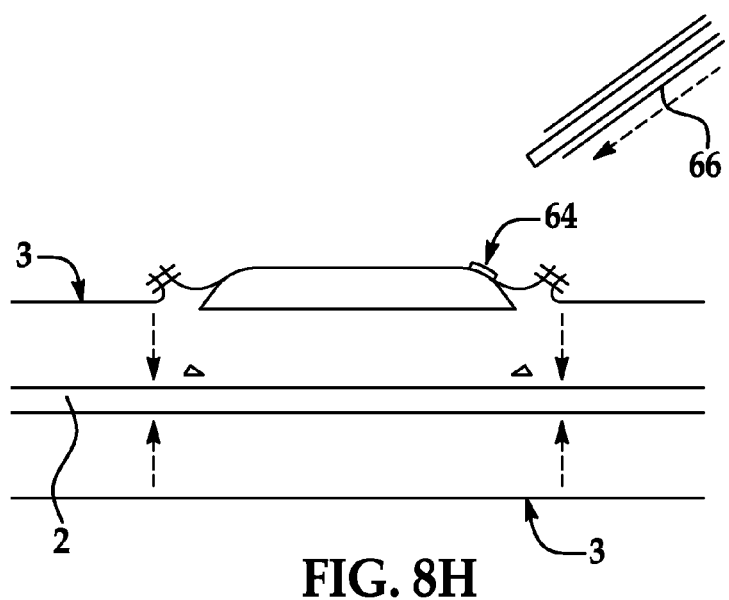
Figure 8I:
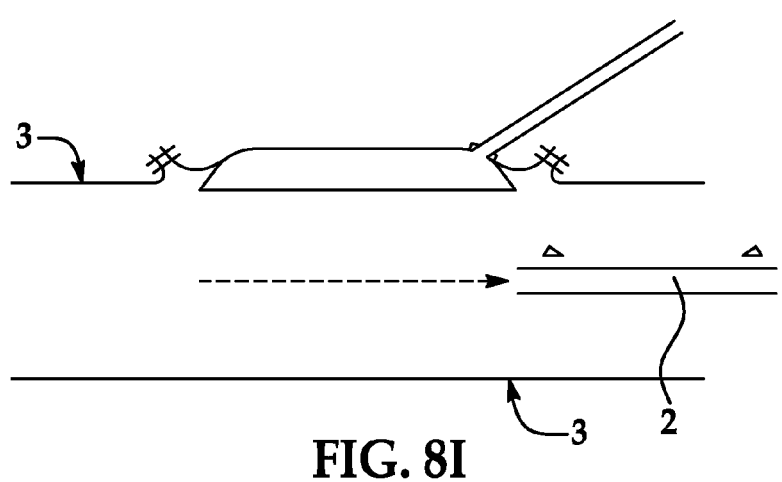
Figure 8J:
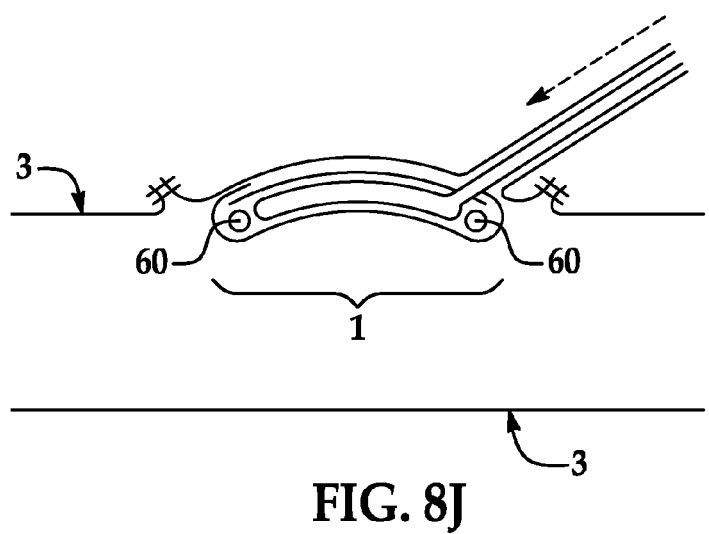

The cardiac assist device wall 58 and skirt 56 are then everted through the aortotomy illustratively as depicted in FIG. 7. A support 60, optionally elliptical or ring shaped, is inserted via an access channel to support the edges of the assist device. An active pumping chamber 62 is then inserted into the device. The shunt is removed and the original aortotomy is repaired.

The support of the present invention can be made from conventional structural shape memory biomaterials such as metals or polymers. In terms of shape memory metals, those materials set forth in U.S. Pat. No. 5,954,725 and U.S. Publication No. 2007/0088436, the entire contents of which are incorporated herein by reference for their teaching of memory metals, are optionally used, including, but not limited to alloys of copper and zinc, nickel titanium, silver and cadmium, and other metals and materials, including nitinol.

The access channel of the cardiac assist device is illustratively introduced by thoracoscopically retrieving an access port on the extra-aortic side after the eversion sequence and then thoracoscopically connecting an extension of the access channel.

Deployment of a cardiac assist device as per either the linear or elliptical endo-aortic component optionally includes preassembly of the endo-aortic component with the cardiac assist device and reversible association with a removable shunt at a position optionally defined by a cradle 54. A complex is formed so that a single delivery of the shunt, the cardiac assist device, and the endo-aortic component into the lumen of an aorta is achievable by a single surgical insertion.

When a fastener includes a separable or separate endo-aortic component and extra-aortic component, a different sequence of deployment is optionally used as depicted in FIG. 8. Prior to insertion of the cardiac assist device, a shunt 2 is optionally in a collapsed configuration whereby the outer dimensions of the shunt 2, cardiac assist device 1 and endo-aortic component 4 including an actuator 48 are sufficiently smaller than the lumen of the aortal position into which the cardiac assist device is placed. The endo-aortic component that includes a folded cardiac assist device 1 is inserted within the lumen of the aorta, optionally the descending thoracic aorta, prior to, simultaneous with, or subsequent to delivery of a shunt 2. (FIG. 8A) After the shunt and endo-aortic component are in position, the actuator 48 deploys the alignment devices 46 and is subsequently detached and removed. (FIG. 8B) The shunt 2 is expanded moving the endo-aortic component and cardiac assist device 1 toward the aortic wall such that the alignment devices 46 pierce the wall and extend beyond the outer surface of the aorta 3. (FIG. 8C) Expansion of a shunt 2 is performed by any method known in the art, illustratively by balloon expansion, return to a memory position of the shunt itself, or other method known in the art.

The extra-aortic component is optionally inserted into the patient thoracoscopically. (FIG. 8D) The extra-aortic component is positioned at the location of the cardiac assist device 1 by associating with the deployed alignment devices 46 extending beyond the outer portion of the aortic wall. The extra-aortic component is then associated with the endo-aortic component and placed into proper aligned position by inserting the alignment devices 46 into the locking mechanism of the extra-aortic component. (FIG. 8E) The alignment devices 46 optionally contain a lock 50, illustratively a slot, barb, or other configuration, which is operable for locking or otherwise associating the extra-aortic component to the endo-aortic component via the alignment devices. (FIG. 8F) This association of the extra-aortic component and the endo-aortic component assures proper positioning between the plateaus or anvil portions of the endo-aortic component and the staples and/or staple shuttles of the extra-aortic component.

An aortotomy is created by movement of a staple shuttle 44 about the shape of the extra-aortic component. (FIG. 8F) Optionally, each staple shuttle 44 serves to attach or otherwise affix the aortic wall to the cardiac assist device simultaneous with the creation of the aortotomy. Alternatively, a staple shuttle creates an aortotomy while moving in one direction and then is reversed in direction for deployment of staples to affix the cardiac assist device to the aortic wall. The aortotomy or other deployment of the staple shuttles optionally does not occur until after the extra-aortic component and the endo-aortic component are in a locked or otherwise associated position.

After the cardiac assist device 1 is attached to the aortic wall, the endo-aortic component and the extra-aortic components are thoracoscopically retrieved via the aortotomy (FIG. 8G), optionally as a single unit. A foldable cardiac assist device 1 is then deployed to the extra-aortic position for subsequent operation. (FIG. 8H) An access channel 66 is introduced, optionally thoracoscopically, and associated with the access channel port 64 of the cardiac assist device 1. (FIG. 8I) Prior to this, simultaneous, or subsequent to the association of the access channel 66 to the access channel port 64, the shunt 2 is collapsed and removed from the aorta, optionally by the same route from which it was introduced. (FIG. 8I) A support 60 is introduced via the access channel and expanded throughout the cardiac assist device. (FIG. 8J) The support confers rigidity to the rim geometry of the cardiac assist device. An active pumping chamber 62 is then introduced also via the access channel 66 and connected to a pumping mechanism.

An inventive fastener is intended to be associated with and useful for deployment of a cardiac assist device or other device intended to be associated with a tubular organ or portion thereof. As such, an inventive cardiac assist device is also provided. A basic cardiac assist device system or the prior art, as shown in FIG. 9, consists of a pumping chamber 62 sutured into the wall of the aorta; an access channel 66 connecting the pumping chamber 68 to a percutaneous access device ("PAD"), a through-the-skin port that permits power, electrical signals and fluid (typically air) to pass between the pumping chamber 62 and a fluid pump 68. These prior art cardiac assist devices commonly possess a rigid or semi-rigid back 72 that provides support for the pumping chamber during operation.

An improved cardiac assist device is provided that, in contrast to prior art devices, has the capability of being delivered using minimally invasive techniques, yet when deployed has sufficient rigidity to provide extended use absent failure. An embodiment of a cardiac assist device of the present invention is depicted in FIG. 10. A flexible extra-aortic wall 74 serves as an outer portion of a housing and is associated with a flexible endo-aortic membrane 76 serving as an inner surface of the housing to form a housing with sufficient flexibility to be folded, compressed, or otherwise reduced in size and to associate with a delivery device such as a fastener as described herein. This flexibility of the housing allows the cardiac assist device to match the contour of a typical human aorta better than prior art pumps. This flexibility also allows the housing to share more of the stress caused by the cycling with the pumping chamber 62 and endo-aortic membrane 76.

After the device is in place, a support 60 is introduced via an access channel 66 and deployed within the housing to increase the rigidity of the resulting cardiac assist device and maintain a shaped configuration during operation. It was discovered by the inventors that cardiac assist devices of the prior art made from semi-rigid material were prone to failure due to unexpected creasing of the back. This was subsequently replaced with a rigid back, yet these systems could not be delivered by minimally invasive techniques. The inventors unexpectedly discovered that supporting the outer geometry of a flexible device is sufficient to prevent failure resulting from microperforations due to membrane deformation, or "creasing," during inflation-deflation cycles without the need for a wholly rigid back. As such, a support 60 provides rigidity to this outer geometry and can be delivered by minimally invasive techniques, thus improving patient outcome.

The endo-aortic membrane 76 is flexible, thin walled and bonded to the outer or inner surface the wall 74. Known solvent bonding techniques such as chlorinated solvent welding of polymers result in the membrane 76 and the wall 74 becoming what is in effect a unitary structure, but for purposes of explanation, the membrane 76 and the wall 74 are drawn in FIGS. 10 and 11 as separate components.

The outer surface of the membrane 76 which, when implanted, interfaces with the blood in the aorta is optionally provided with fibrils, forming a textured surface similar to a flocking, to promote cellular adhesion in forming a pseudointima on the outer surface of the membrane 76.

The membrane 76 is optionally configured to enhance the durability of the blood pump by being formed with geometry such that even without an applied pressure or vacuum (that is, without any significant pressure differential from one side of the membrane to the other), membrane shape generally matches that of a curved inner surface of an extra-aortic wall or the anatomy of the site of device operation. This curved membrane is formed on a curved surface. This curved membrane experiences less creasing during the inflation-deflation cycles, as compared to flat membranes. Practical experience has shown that flat membranes crease at certain cusp points when they transition between inflated and deflated states. Analyses and testing indicate that the curved membrane reduces the magnitude and occurrence of this creasing problem.

A cardiac assist device or any portion thereof is constructed from any number of biocompatible materials suitable for surgical implantation. Biocompatible materials illustratively include polyurethane, fluoropolymers, polyamides, silicone, rubber, nitrile (e.g. acrylonitrile (ACN) and butadiene), and polyvinylchloride.

A pumping chamber 62 is then, optionally, inserted into the housing via the access port to provide a closed chamber for inflation and deflation cycles during operation of the device. It is appreciated that a pumping chamber and a housing need not be separate elements. A housing has the capability of acting as a pumping chamber itself. The presence of a pumping chamber allows separation of the support from the internal structure of the pumping chamber.

An anastomotic skirt 56 is optionally provided with a first portion associated with the housing at the outer surface and having a second portion that is unattached to the outer surface of the housing to create a flange that optionally serves as a suture ring. An additional material strip, such as a pledget 18, is optionally secured to the flange by for example stitching, adhesive or other, for implanting the device in an incision in the aorta by means of sutures, staples, adhesive, or other affixment known in the art. It is appreciated that in some embodiments the affixment used to affix the assist device is optionally the same affixment used to attach a pledget to a second portion of a skirt, or is different therefrom. The pledget 18 optionally has a fibrous surface allowing body tissues to migrate into, and mechanically interweaving with the pledget, to augment the sealing action initially established by the surgical implantation sutures between the flange and the wall of the aorta. The skirt 56 and pledget 18 are made of various appropriate materials, such as polyester, which are commercially available and are appropriate for use in implanted devices.

To facilitate surgical explanation of the device, the outer surface of the skirt 56, or portion thereof such as a first portion optionally includes an overlayer made of a substance to which tissue does not adhere or adheres only minimally. Optionally, the skirt itself is made from a material from which tissue does not adhere or adheres only minimally. Biocompatible substances prohibiting cellular adhesion illustratively include fluoropolymers and silicone. The biocompatible substances prevent scar tissue from adhering to the skirt so the cardiac assist device can be explanted if desired.

Figure 11A:
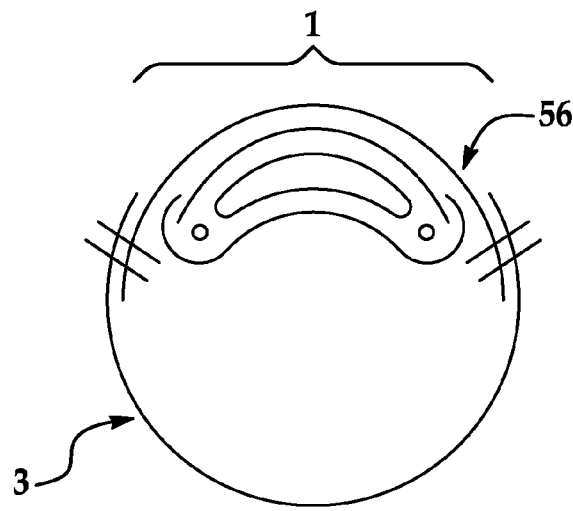
FIG. 11 illustrates various overlaps between a skirt and an aorta wall for affixing a cardiac assist device.
Figure 11B:
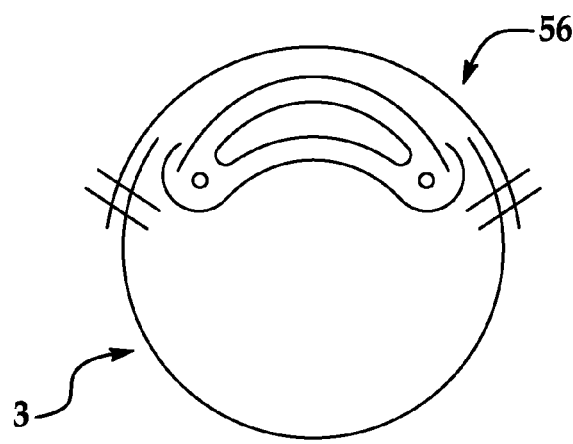
Figure 11C:
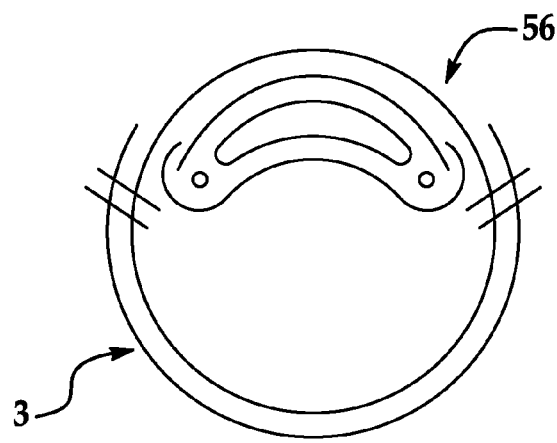

FIG. 10C depicts the skirt 56 stapled to the wall of an aorta 3 at the site of aortonomy with the staple point everted. In other embodiments as depicted in FIG. 11, the association between the cardiac assist device 1 and the aortic wall 3 creates an overlapping configuration. This association eliminates the everted aortal cardiac assist device anastomotic line generally observed in FIG. 10C. These configurations represent particularly relevant advances in the art that greatly simplifies attaching a cardiac assist device to an aortonomy and provides a highly secure junction. Several overlapping configurations are possible when an inventive fastener is used to deploy a cardiac assist device. Configuration 2D illustrates an overlap where the aortic wall overlies the skirt, flange, or other attachment point of a cardiac assist device. Alternatively, as depicted in configuration 2E, the aortic wall is fastened inside the fabric skirt in an overlapping configuration. Configuration 2F as depicted in FIG. 11 illustrates a continuous circumferential fabric skirt as part of a cardiac assist device that allows a similar overlapping configuration between the aortic wall and the cardiac assist device. These configurations are achievable by altering the directionality of the skirt and the edge of the aortonomy prior to engaging the inventive fastener, or simply by use of a foldable cardiac assist device.

The overlapping configurations between the fabric skirt and the aortic wall allow multiple methods of affixing the two. In these embodiments, the traditionally required everted anastomotic line is not present. In some embodiments, staples or sutures are used to affix the cardiac assist device to the aortic wall. Alternatively, a mushroom fastener or rivet is used. Optionally, a surgical adhesive is used to attach a cardiac assist device to the aortic wall. Any surgical adhesive or fastener known in the art is operational herein. Illustratively, an adhesive is a one part or two part biologically compatible material. One type of adhesive that is currently available is a cyanoacrylate adhesive. Alternatively, fibrin sealants or other natural materials are employed. Other sealants such as those described in U.S. Patent Application Publication 2007/0129505, the contents of which are incorporated herein by reference, are operable to adhere a cardiac assist device to the aortic wall.

An overlapping configuration is optionally created by inserting a cardiac assist device by invasive or minimally invasive delivery. In some embodiments, an overlapping configuration is achieved by providing an endo-aortic component that has one or more slots transcending or within the longitudinal direction of the component such that preloading of the cardiac assist device onto an endo-aortic component includes threading of the terminal ends of the fabric skirt through the slots so they extend outwardly over the plateaus of the endo-aortic component. Upon affixing the cardiac assist device to the aorta and eversion, an overlapping configuration is achieved.

A cardiac assist device is optionally provided with sufficient air or other fluid in the housing such that an air pocket is formed between the membrane 76 and the edge of the support 60 when the blood pump is in a deflated state to reduce the stress on the membrane during the cyclical operation of the pump. The support has a membrane-contacting region that typically contacts the portion of the membrane when the pump is deflated. The membrane 76 optionally does not contact the support 60 around the entire cross-sectional diameter of the support, due to air pockets which form in proximity to the support circumference during the deflation cycle. By placing and heat setting the membrane on a large bead edge forming platen having a platen footprint substantially identical to the final geometry of a support 60, a looped membrane edge complementary to the support curvature results as a preformed membrane. Employing the resulting membrane preform with a relatively smaller support 60, during deflation, the maximal linear span of curvature for the looped membrane edge creates an air pocket as the membrane preform wraps around the support and is larger than the maximal linear extent of the support.

In order to further reduce localized stresses on the membrane 76 during the deflation cycle, the diameter D2 of the air pocket created by the membrane 76 is always greater than the support diameter D1. In other words, D2>D1. The air pocket increases the radius of curvature of the membrane 76 near the support 60, thus, reducing the strain on the membrane 76 during inflation-deflation cycles.

The delivery of a cardiac assist device is not limited to any single portion of the aorta. The inventive fastener and cardiac assist devices are optionally used or positioned within the ascending aorta, the aortic arch or the descending aorta. The invention is operable for delivery of a cardiac assist device in the descending thoracic aorta.

It is further appreciated that the linear or planar orientations of several embodiments are alterable to accommodate the anatomy of the site of use. Illustratively, the staple anvil and staple magazine are optionally curved similar to the curve of the aortic arch. In other embodiments, the fastener is curved optionally at a distal end and is linear optionally at the proximal end allowing more optimal use at a region that includes the ascending or descending aorta and the aortic arch.

The individual components of the inventive fastener are appreciated to be repositionable relative to one another in any operable manner. The connections, orientations, shapes, and associations illustrated herein are for illustrative purposes only and are not meant to be a limitation on the construction of the fastener or cardiac assist device. It is appreciated that a staple magazine and anvil need only be positioned on opposing faces of an aortic wall such that staples or other attachment device will pierce the aortic wall when deployed.

The disclosures of the following patent documents are hereby incorporated by reference in their entirety: U.S. Pat. Nos. 4,051,840; 4,630,597; 4,692,148; 4,733,652; 4,809,681; 5,169,379; 5,761,019; 5,833,619; 5,904,666; 6,042,532; 6,132,363; 6,471,633; 6,511,412; 6,735,532; 7,374,531; 7,468,050 and U.S. patent application Ser. Nos. 10/770,269; 10/865,965; 11/178,969; 11/679,487; and 60/709,323. This incorporation is as if each patent and application were expressly placed into this application for each word, number, and figure presented therein.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A cardiac assist device adapted for placement in an incision in an aorta wherein a part of the assist device after placement is in contact with blood passing through the aorta and is inflated and deflated to provide left ventricular assistance, the assist device comprising:
    a foldable elongate housing comprising a flexible extra-aortic wall associated with a flexible endo-aortic membrane and without a wholly rigid back, the flexibility allowing the cardiac assist device to be folded without creating a crease, and preserving topologic relationships between a set of components of the cardiac assist device;
    a discrete stiffener present within said housing to increase the housing rigidity versus the housing rigidity without the stiffener and defining the outer dimensions thereof, wherein the extra-aorta wall has a rigidity insufficient to independently maintain a shaped configuration sufficient for operation without the stiffener;
    an airtight pumping chamber located within said housing and in fluid communication with a region external to said device; and
    wherein the flexible endo-aortic membrane has a blood contacting part of the cardiac assist device which, after placement, is in contact with blood passing through an aorta and is inflatable and deflatable to provide left ventricular assistance.

2. The device of claim 1 further comprising a percutaneous access device disposed external to said pumping chamber along an access channel.

3. The device of claim 2 further comprising a fluid pump in fluid communication with said pumping chamber along said access channel.

4. The device of claim 1 further comprising a skirt having a first portion attached to the outer surface of said housing, and a second portion that is unattached to the outer surface of the housing, the unattached area forming a suture ring for attaching the assist device to the aorta of a patient.

5. The device of claim 4 further comprising an overlayer nonadherent to scar tissue on an exposed surface of said skirt.

6. The assist device of claim 1, wherein said flexible aortic wall and said flexible endo-aortic membrane are curved to generally match the contour of a portion of the aorta.

7. The assist device of claim 1 wherein said membrane edge is preformed and looped with a maximal linear span of curvature that is greater than the maximal transverse linear extent of said support, wherein said housing includes a sufficient amount of fluid to form an air pocket intermediate between the support and said membrane during deflation of said assist device.

8. The assist device of claim 4 associated with a fastener for attaching a cardiac assist device to an aorta, the fastener comprising:
    an anvil and a staple magazine, where said staple magazine is removably or fixedly connected to said anvil; and
    a deployment mechanism, said deployment mechanism removably or fixedly connected to said anvil or said staple magazine, said anvil or said staple magazine associated with the cardiac assist device prior to deploying the cardiac assist device; and
    wherein said association creates an everted anastomotic line when said device is deployed at an aortic wall.

9. The assist device of claim 8 wherein said skirt and said aortic wall are evertable and said association creates an overlap between said skirt and said aortic wall at an anastomotic line when said device is deployed at an aortic wall.

10. The assist device of claim 9 wherein said overlap is formed by the aortic wall overlying at least portion of said skirt.

11. The assist device of claim 9 wherein said overlap is formed by the skirt overlying said aortic wall.

12. The device of claim 1 wherein the stiffener is elliptical or ring shaped.

13. The device of claim 1 wherein the stiffener is an insertable support, the insertable support having a rigidity sufficient to increase the rigidity of the cardiac assist device over that of the extra-aortic wall without the insertable support.

* * * * *